United States Patent [19]

Buchanan

[11] 4,415,980
[45] Nov. 15, 1983

[54] AUTOMATED RADIOGRAPHIC INSPECTION SYSTEM

[75] Inventor: Robert A. Buchanan, Palo Alto, Calif.

[73] Assignee: Lockheed Missiles & Space Co., Inc., Sunnyvale, Calif.

[21] Appl. No.: 239,611

[22] Filed: Mar. 2, 1981

[51] Int. Cl.³ .......................... G06F 15/46; H04N 5/32
[52] U.S. Cl. ..................................... 378/58; 358/111; 364/414; 378/99; 378/4; 378/21
[58] Field of Search ............... 364/414, 515, 521, 522, 364/525, 527; 358/111, 166; 378/2, 44, 51, 58, 62, 98; 250/323, 321

[56] References Cited

U.S. PATENT DOCUMENTS

| | | | |
|---|---|---|---|
| 3,588,502 | 6/1971 | Greenfield | 356/156 X |
| 3,673,394 | 6/1972 | Hartmann | 364/300 X |
| 3,988,602 | 10/1976 | Gorsica, Jr. | 364/515 |
| 4,024,225 | 5/1980 | Mistretta | 358/111 |
| 4,056,716 | 11/1977 | Baxter et al. | 364/515 |
| 4,092,537 | 5/1978 | Stewart | 250/314 |
| 4,323,973 | 4/1982 | Greenfield | 358/111 X |
| 4,335,427 | 6/1982 | Hunt et al. | 364/414 |

Primary Examiner—Edward J. Wise
Attorney, Agent, or Firm—John J. Morrissey

[57] ABSTRACT

In an automated real-time radiographic inspection system for detecting flaws, defects or inhomogeneities in manufactured objects, the objects (10, 11, 12, ...) to be tested are moved on a conveyor (20) in succession past an X-ray source (30). Penetrating X-ray radiation is transmitted through the objects (10, 11, 12, ...) to cause an image to be formed for each object in succession by an electronic imaging system (40). The imaging system (40) generates digital signals representative of the image for each object, and transmits the digital signals to a data processor/comparator (50). One of the objects (10, 11, 12, ...) may be considered as a reference object against which the other objects are compared for structural homogeneity. Thus, the electronic images of the objects (11, 12, ...) could be compared with the electronic image of, for example, the object (10). Alternatively, the electronic images of the test objects could be compared with an electronic reference image programmed into the data processor/comparator (50), the programmed reference image. The comparison performed by the data processor/comparator (50) is a subtraction process, which eliminates background features common to test and reference images. Thus, any flaw appearing in a test image, but not present in the reference image, stands out in sharp detail. When a flaw occurs in a test image, the subtractive process results in a non-null signal, which activates a conveyor control mechanism (70) for stopping the conveyor (20) so as to enable rejection of the flawed test object.

11 Claims, 5 Drawing Figures

AUTOMATED RADIOGRAPHIC INSPECTION SYSTEM

TECHNICAL FIELD

This invention pertains generally to radiographic inspection for quality control in industrial applications. In particular, this invention pertains to automated real-time X-ray inspection of manufactured goods by image subtraction.

BACKGROUND ART

Conventionally in industrial radiographic inspection, a beam of high-energy X-ray radiation is transmitted through a test object to be inspected, and an image of the test object is formed by interaction of the transmitted radiation with silver halide in a photographic film. A flaw, defect or structural inhomogeneity in the test object is detected by examining (or "reading") the X-ray image formed on the photographic film. The reading of X-ray images on photographic film, however, is inherently a subjective procedure, and is subject to idiosyncratic variations depending upon the skill and knowledge of the individual human agent who does the reading. Furthermore, the requirement that the photographic film be chemically developed in order to form the image precludes real-time inspection of the test object.

Image subtraction procedures have not generally been used in industrial radiographic inspection. In clinical radiology, on the other hand, image subtraction procedures have been used since the 1930's for suppressing the appearance of bony structures overlying anatomical regions of interest. With image subtraction techniques used in clinical radiology, two images of the region of interest are formed in sequence. The images may be formed by chemical means (i.e., on photograhic film) or by electronic means. The first image is representative of the region of interest in its natural state, and the second image is formed after a radiopaque medium has been injected into the region. If the position of the region of interest relative to the X-ray source and relative to the image-forming means (i.e., photograhic film or electronic image-forming device) remains the same for the first and second images, subtraction of one of the images from the other to form a subtractive image leaves only the radiopaque medium to be seen. Thus, by studying the subtractive image, one can view an outline of the region of interest (as defined by the radiopaque medium) in sharp contrast with surrounding tissue.

An image subtraction procedure described in an article entitled "A Multiple Image Subtraction Technique for Enhancing Low Contrast, Periodic Objects" by C. A. Mistretta et al., *Investigative Radiology*, Vol. 8, No. 1, (1973), pp. 43-49, uses electronic image forming means and eliminates the need for injecting a radiopaque medium into the region of interest. In the procedure described by Mistretta et al., X-ray transmission differences associated with periodic mass changes that occur in certain tissues are used to form subtractive images in which background anatomical structures are suppressed. More particularly, the procedure described by Mistretta et al. takes advantage of the time-dependent variation in blood mass distribution between systolic and diastolic states of pulmonary arteries to generate arteriograms by an electronic image subtraction technique.

In industrial radiography, manufactured articles, which do not undergo time-dependent internal structural changes, have not heretofore been considered amenable to radiographic inspection by image subtraction procedures.

SUMMARY OF THE INVENTION

It is an object of the present invention to provide a radiographic inspection system for industrial quality control using an electronic image subtraction technique.

More particularly, it is an object of the present invention to provide a real-time X-ray inspection system having automated accept/reject capability for quality control in industrial applications.

It is a further object of the present invention to provide a radiographic inspection system that uses an image subtraction procedure for background suppression and edge enhancement in order to detect low-contrast defects or inhomogeneities in manufactured articles.

One automated image subtraction procedure in accordance with the present invention includes: (1) forming an X-ray image of a reference object by electronic means; (2) forming X-ray images of each one of a plurality of test objects in succession by electronic means; and (3) electronically subtracting the image of each test object from the image of the reference object so that if a non-null difference between the image of a particular test object and the image of the reference object occurs, a mechanism is activated for automatically rejecting that particular test object. The above-described image subtraction procedure could be adapted to inspect only a portion, or several different portions, of a test object rather than the entire test object. Thus, X-ray images of corresponding portions of the reference and test objects could be formed and electronically subtracted in accordance with this invention to enable inspection of desired portions of the test object.

Another image subtraction procedure in accordance with the present invention includes forming an initial electronic X-ray image of the object to be tested; and thereafter displacing either the test object, or the X-ray source, or the image-forming device with respect to the position at which the initial image was formed, and then forming a second (or "displaced") image of the test object. The displaced image is then subtracted electronically from the initial image to form a subtractive image. Any flaw, defect or structural imhomogeneity in the test object then appears in the subtractive image in sharp detail, because the background common to the initial and displaced images has been eliminated from the subtractive image. In an automated inspection system in accordance with the invention, the occurrence in the subtractive image of a flaw, defect or structural inhomogeneities of a selected shape and/or magnitude can be used to cause automatic rejection of the test object.

In a variation of the displaced image procedure, a test object of large size (e.g., a rocket motor) is continuously rotated in the space between the X-ray source and the image-forming device, and different portions of the test object are imaged in succession and subtractively compared to determine whether any defects or inhomogeneties exist. A more detailed discussion of the application of the image subtraction technique of the present invention for inspecting rocket motors is found in "X-Ray System Inspects Rocket Motors" by B. M.

Elson, *Aviation Week & Space Technology* (Aug. 25, 1980), pp. 72-77.

BEST MODE OF CARRYING OUT THE INVENTION

Figure 1:
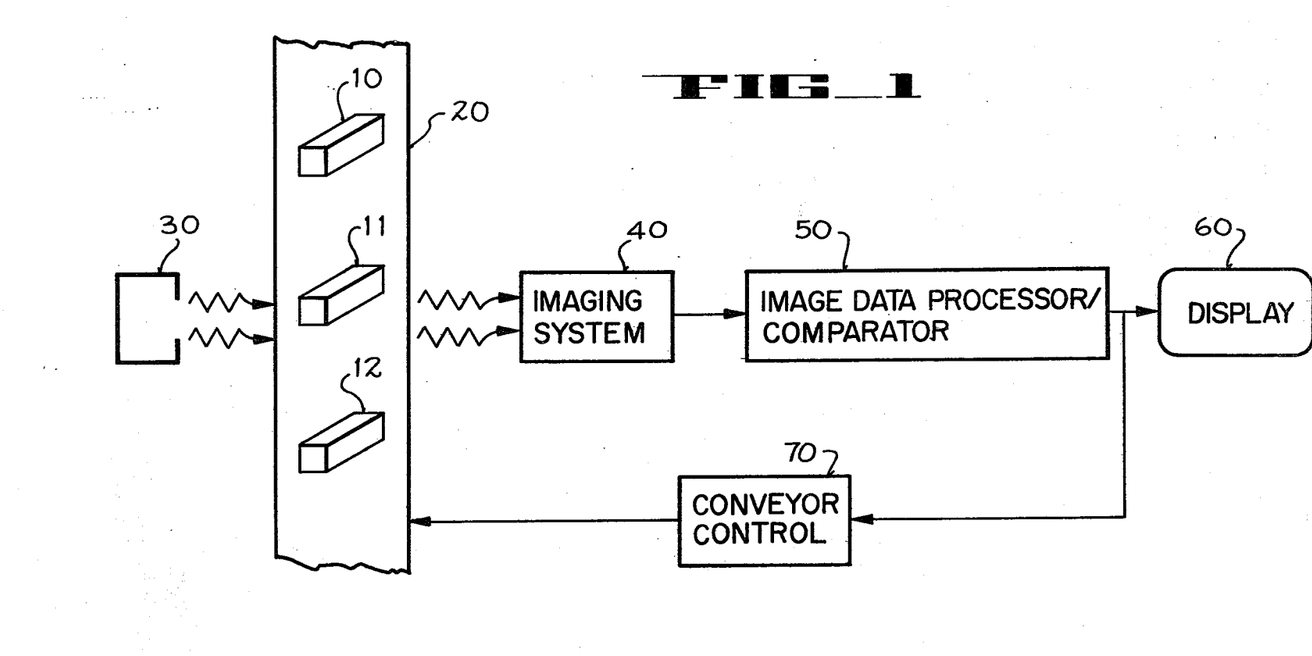
FIG. 1 is a schematic illustration of a radiographic inspection system according to the present invention.

In the radiographic inspection system illustrated in FIG. 1, industrially manufactured objects 10, 11, 12, . . ., which are intended to be structurally identical, are positioned on a moving conveyor 20 so as to be irradiated in sequence by penetrating electromagnetic radiation emitted by a source 30. The penetrating radiation is X-ray radiation in the preferred embodiment, although in principle gamma radiation could be used.

Radiation transmitted through each one of the objects 10, 11, 12, . . . causes an image of the object to be formed by an electronic imaging system 40. The imaging system 40 generates digital signals representative of the image for each object, and transmits the digital signals to a data processor/comparator 50. One of the objects, e.g., the object 10, may be used as a standard or reference against which the other objects are compared. Thus, the digital signals constituting the electronic image of the object 10 can be stored in the data processor/comparator 50, and the subsequently generated digital signals constituting the electronic images of the other objects 11, 12, . . . can be compared in sequence with the signals constituting the image of the object 10. Alternatively, an electronic image of a standard or reference object can be programmed into the data process/comparator 50, and electronic images of the objects 10, 11, 12, . . . can be compared in turn with the reference image stored in the data processor/comparator 50.

In accordance with the present invention, the data processor/comparator 50 subtracts the electronic image of a test object from the stored electronic image of the reference object. If the structure of the test object conforms exactly to the structure of the reference object, the resulting subtractive image is a null image. However, if there is a structural flaw in the test object, the resulting subtractive image shows the flaw in sharp detail because the structural features that the test object has in common with the reference object are suppressed by the image subtraction process.

The subtraction image produced by the data processor/comparator 50 can be shown visually for each test object in succession on a display device 60. A human operator viewing each subtractive image shown on the display device 60 can make a judgement as to whether a flaw appearing in any particular image is of sufficient significance to warrant rejection of the test piece exhibiting the flaw. Alternatively, the data processor/comparator 50 can be programmed so that the occurrence of a non-null subtractive image of any pre-selected size, shape or location on a test object automatically causes rejection of the test object generating that non-null subtractive image. As shown in FIG. 1, the occurrence of a non-null subtractive image causes a signal to be transmitted from the data processor/comparator 50 to a conveyor control mechanism 70 for stopping the movement or changing the direction of the conveyor 20 so as to implement the rejection of the test object generating the non-null subtractive image. As another alternative, the occurence of a non-null subtractive image could activate a means for marking the test object generating the non-null subtractive image, so that the flawed test object can be identified for rejection.

Figure 2:
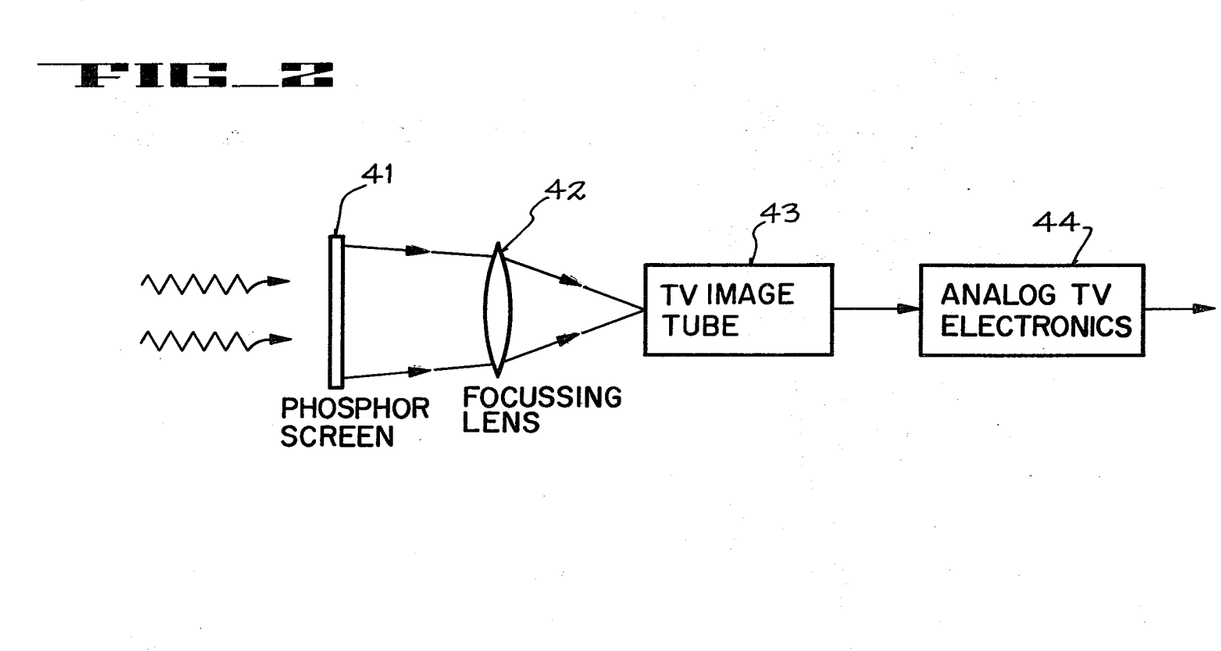
FIG. 2 is a schematic illustration indicating component equipment of the imaging means shown in FIG. 1.

The electronic imaging system 40 of FIG. 1 may be conventional as shown in FIG. 2. Thus, the radiation transmitted through a test object impinges on a phosphor screen 41 to generate visible light signals indicative of the internal structure of the test object. The visible light signals are focussed by a lens 42 onto a television image tube 43, which is coupled by means of conventional analog electronics 44 to the data processor/comparator 50 shown in FIG. 1.

Figure 3:
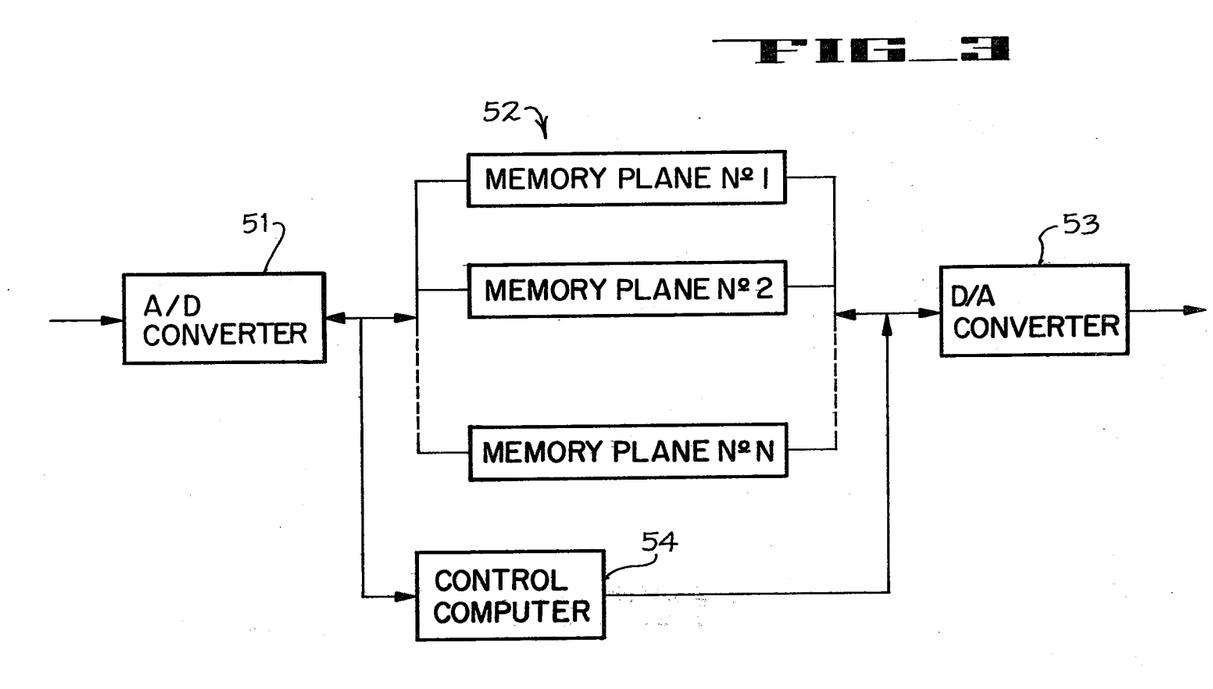
FIG. 3 is a schematic illustration indicating component equipment of the processor/comparator means shown in FIG. 1.

The data processor/comparator 50 of FIG. 1 may likewise be conventional, such as a De Anza digital image processor Model 1032L1. As shown in FIG. 3, analog signals generated for each test object by the electronics 44 of the imaging system 40 are converted to digital signals by an analog-to-digital convertr 51. The digital signals constituting the electronic image for each test object are then stored in an appropriate memory plane in a data processor portion 52 of the data processor/comparator 50. There are N separate memory planes (i.e., memory planes 1, 2, . . . , N) shown in the data processor/comparator 50 of FIG. 3. According to a simple programming technique, memory plane 1 may be used to store the digitized image of the reference object, memory plane 2 may be used to store the digitized image of the test object, and memory plane 3 may be used to store the subtractive image of the reference and test objects for subsequent imput to a comparator portion of the data processor/comparator 50, such as a control computer 54. It is to be recognized, however, that other programming techniques could be developed to take more efficient advantage of the particular architectural features of the data processor/comparator 50.

The control computer 54 is programmed to subtract the electronic image for the reference object from the electronic image for each test object in succession so as to produce a subtractive image for each test object. Each subtractive image comprises digital signals, which are converted to analog signals by a digital-to-analog converter 53 for activating the display device 60 and/or the conveyor control mechanism 70.

The schematic representation in FIG. 3 indicates functional capabilities rather than structural components of the data processor/comparator 50. Depending upon the architecture of the system, control functions to be performed by the control computer 54 could include: (1) integration of TV frames formed on the television image tube 43 to produce a single integrated radiographic image for each test object; (2) subtraction of one digitized image from another digitized image in the memory of the data processor portion 52, and retention in the memory of the subtractive image so formed; (3) analysis of a subtractive image to provide a quantitative assessment of the significance of any flaw, defect or structural inhomogeneity generating a nonnull subtractive image; and (4) implementation of "accept" or "reject" decisions based upon predetermined accept/reject criteria.

Figures 4, 5:
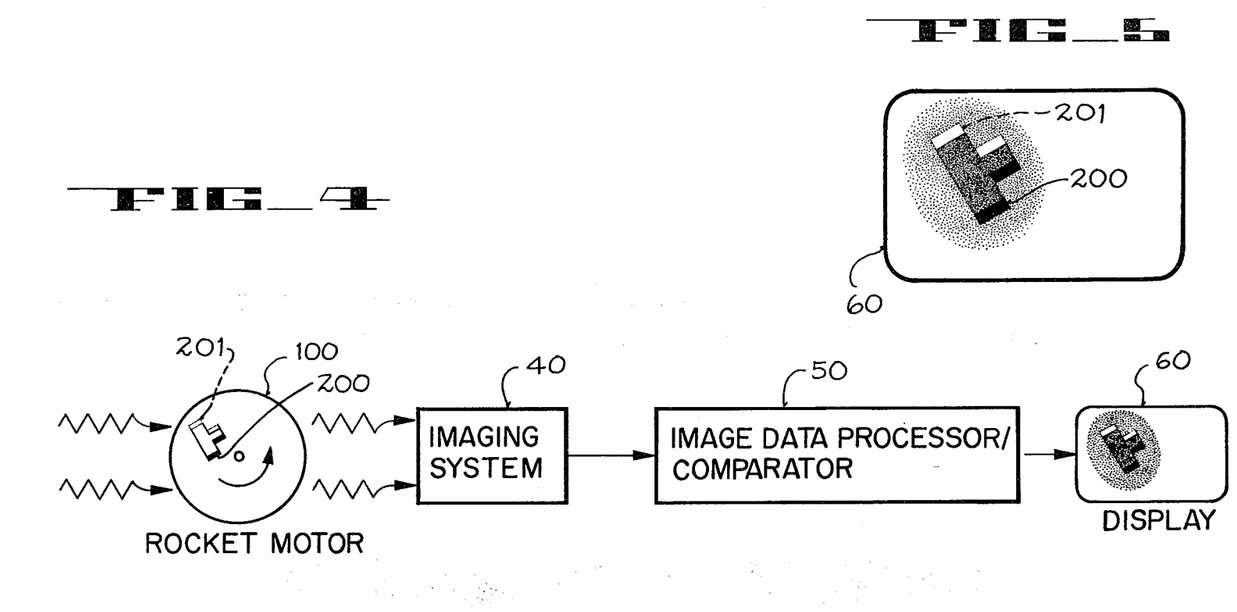
FIG. 4 is a schematic illustration of a radiographic system according to the present invention for inspecting a rocket motor.
FIG. 5 is a blown-up representation of a subtractive image observable on the display means of the system shown in FIG. 4.

An application of the present invention for inspecting large symmetrical test objects such as rocket motors is shown in FIG. 4. A cylindrically configured rocket motor 100, which has an internal inhomogeneity or flaw with a contour 200, is mounted so as to be rotatable about its cylindrical axis. X-ray radiation transmitted through the rocket motor 100 in a stationary first position causes the imaging system 40 to produce an electronic image, which is transmitted as a "reference" image to the data processor/comparator 50. The rocket motor 100 is then rotated through a small angle to a stationary second position at which the new location of the inhomogeneity's contour (as shown in phantom in FIG. 4) is indicated by the reference number 201. The displacement of the second position contour 201 from the first position contour 200 is no greater than the maximum dimension that can be tolerated for any inhomogeneity or flaw that may be present in the rocket motor 100. X-ray radiation transmitted through the rocket motor 100 in the second position causes the imaging system 40 to produce an electronic image, which is transmitted to the data processor/comparator 50 as a "test" image.

The data processor/comparator 50 performs a digital subtraction of the "test" image from the "reference" image (or vice versa) to produce a subtractive mage, which appears on the display device 60. Preferably, the angle of rotation of the motor 100 is small enough so that the contour 201 is displaced from the contour 200 just enough to preclude subtraction of one contour from the other by the subtractive process. Since the second position contour 201 does not coincide with the first position contour 200, the subtractive process, which suppresses the common background features appearing in both the "reference" and "test" images, causes the contours 200 and 201 to be displayed in sharp detail. A blown-up representation of the subtactive image visually appearing on the display device 60 is shown in FIG. 5, which provides an indication of the clarity and fineness of definition that is possible with a radiographic inspection system according to the present invention.

This invention has been described above in terms of particular embodiments and applications. However, other embodiments and applications for the present invention would be apparent to workers skilled in the art upon perusal of the above description and the accompanying drawing. Therefore, the above description is to be considered merely as illustrative of the invention. The invention is defined by the following claims and their equivalents.

I claim:

1. A method of determining structural conformity of a test object to a reference object for quality control of manufactured objects, said method comprising the steps of:
   (a) transmitting X-ray radiation through said reference object to phosphor means for generating an optical signal, which is converted to an electronic image of said reference object;
   (b) transmitting x-ray radiation through said test object to phosphor means for generating an optical signal, which is converted to an electronic image of said test object; and
   (c) subtracting one of the aforesaid electronic images from the other to produce a subtractive image in which any significant structural difference between said test object and said reference object appears in sharp detail.

2. The method of claim 1 wherein said electronic images of said reference and test objects are digitized representations of said reference and test objects, and wherein the subtracting of one of said electronic images from the other is performed by computer means.

3. The method of claim 2 wherein the electronic image of said reference object is stored in a memory device, and the electronic image of said test object is compared with said image of said reference object by a process wherein one said images is subtracted from the other.

4. The method of claim 1 wherein a separate electronic image is formed of each one of a plurality of test objects, and wherein a control signal is generated whenever any significant difference appears between a particular one of the test objects and said reference object, said control signal activating means for rejecting said particular one of said test objects as not being in structural conformity with said reference object.

5. A method of detecting a substantial inhomogeneity in a test object, said method comprising the sequential steps of:
   (a) forming a first image of said test object by causing penetrating electromagnetic radiation from a radiation source to pass through said test object and impinge upon a detector;
   (b) causing displacement of one relative to another of said radiation source, test object and detector;
   (c) forming a second image of said test object by causing penetrating electromagnetic radiation from said radiation source to pass through said test object and impinge upon said detector; and
   (d) subtracting one of said first and second images from the other to produce a subtractive mage in which any substantial inhomogeneity in said test object appears.

6. The method of claim 5 wherein a control signal is generated whenever any inhomogeneity in said test object appears in said subtractive image, said control signal activating means for rejecting said test object.

7. The method of claim 5 wherein said test object is moved relative to said radiation source and detector after said first image has been formed.

8. The method of claim 7 wherein said first and second images are formed by causing X-ray radiation that has passed through said test object to impinge upon phosphor means for generating corresponding first and second optical signals, and by converting said optical signals to digital electronic signals constituting said first and second images.

9. The method of claim 8 wherein digital signal constituting said first image are stored in a memory device, and digital signals constituting said second image are compared with said digital signals constituting said first image by a process wherein one of said first and second images is subtracted from the other by computer means.

10. A system for determining structural conformity of a test object to a reference object for quality control of manufactured objects, said system comprising:
   (a) means for transmitting X-ray radiation through said reference object to phosphor means for generating an optical signal, which is converted to an electronic image of said reference object;
   (b) means for transmitting X-ray radiation through said test object to phosphor means for generating an optical signal, which is converted to an electronic image of said test object; and (c) means for subtracting one of said electronic images from the other to produce a subtractive image in which any significant structural difference between said test object and said reference object appears in sharp detail.

11. A system for detecting a substantial inhomogeneity in a test object, said system comprising:

(a) means for forming a first image of said test object by causing penetrating electromagnetic radiation from a radiation source to pass through said test object and impinge upon a detector;

(b) means for causing displacement of one relative to another of said radiation source, test object and detector;

(c) means for forming a second image of said test object by causing penetrating electromagnetic radiation from said radiation source to pass through said test object and impinge upon said detector; and (d) means for subtracting one of said first and second images from the other to produce a subtractive image in which any substantial inhomogeneity in said test object appears.

* * * * *

REEXAMINATION CERTIFICATE (802nd)
United States Patent [19]
Buchanan

[11] B1 4,415,980
[45] Certificate Issued Dec. 29, 1987

[54] AUTOMATED RADIOGRAPHIC INSPECTION SYSTEM

[75] Inventor: Robert A. Buchanan, Palo Alto, Calif.

[73] Assignee: Lockheed Missiles & Space Co., Inc., Sunnyvale, Calif.

Reexamination Request:
No. 90/000,968, Mar. 17, 1986

Reexamination Certificate for:
Patent No.: 4,415,980
Issued: Nov. 15, 1983
Appl. No.: 239,611
Filed: Mar. 2, 1981

[51] Int. Cl.⁴ .......................... G06F 15/46; H04N 5/32
[52] U.S. Cl. ..................................... 378/58; 358/111; 364/414; 378/4; 378/21; 378/99
[58] Field of Search .............. 364/414, 507, 521, 525, 364/527; 358/106, 111, 166; 378/2, 44, 51, 58, 62, 98

[56] References Cited

U.S. PATENT DOCUMENTS

4,364,113  12/1982  Sengebusch et al. ............ 358/106 X
4,392,155   7/1983  Konforti et al. ..................... 358/106

OTHER PUBLICATIONS

Digital Video Systems Applied to Product Inspection, P. Mengers, "Proceedings of the Society of Photo-Optical Instrumentation Engineers," vol. 170 (Optics in Quality Assurance II), (May 9, 1979), pp. 43–50.
High-Speed Digital Image Processing, P. Mengers et al., reprinted from Research/Development, (Oct. 1977).
DS-20 Product Specifications, Quantex Corporation, published pre-1979.
Autoray Automatic Radiographic Inspection Equipment Machinery and Production Engineering, vol. 121, No. 3130, Nov. 8, 1972.
Kruger et al: Industrial Applications of Computed Tomography at Las Alamos Scientific Laboratory. Optical Engineering May/Jun. 1980, vol. 19, No. 3, pp. 273–282.

Primary Examiner—Felix D. Gruber

[57] ABSTRACT

In an automated real-time radiographic inspection system for detecting flaws, defects or inhomogeneities in manufactured objects, the objects (10, 11, 12, ...) to be tested are moved on a conveyor (20) in succession past an X-ray source (30). Penetrating X-ray radiation is transmitted through the objects (10, 11, 12, ...) to cause an image to be formed for each object in succession by an electronic imaging system (40). The imaging system (40) generates digital signals representative of the image for each object, and transmits the digital signals to a data processor/comparator (50). One of the objects (10, 11, 12 ...) may be considered as a reference object against which the other objects are compared for structural homogeneity. Thus, the electronic images of the objects (10, 11, ...) could be compared with the electronic image of, for example, the object (10). Alternatively, the electronic images of the test objects could be compared with an electronic reference image programmed into the data processor/comparator (50), the programmed reference image. The comparison performed by the data processor/comparator (50) is a subtraction process, which eliminates background features common to test and reference images. Thus, any flaw appearing in a test image, but not present in the reference image, stands out in sharp detail. When a flaw occurs in a test image, the subtractive process results in a non-null signal, which activates a conveyor control mechanism (70) for stopping the conveyor (20) so as to enable rejection of the flawed test object.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 5-9 and 11 is confirmed.

Claims 1-4 and 10 are cancelled.

New claims 12-16 are added and determined to be patentable.

12. *A system for detecting a substantial inhomogeneity in a test object, said system comprising:*

(a) *means for forming a first image of said test object by causing penetrating electromagnetic radiation from a radiation source to pass through said test object and impinge upon a detector, said detector thereby generating a first electronic signal, said first electronic signal then being digitized, said digitized first electronic signal being stored in a first memory plane as said first image;*

(b) *means for causing displacement of one relative to another of said radiation source, test object and detector after said first image has been formed;*

(c) *means for forming a second image of said test object by causing penetrating electromagnetic radiation from said radiation source to pass through said test object and impinge upon said detector after said displacement has occurred, said detector thereby generating a second electronic signal, said second electronic signal then being digitized, said digitized second electronic signal being stored in a second memory plane as said second image; and*

(d) *means for subtracting one of said first and second images from the other to produce a subtractive image in which any substantial inhomogeneity in said test object appears.*

13. *The system of claim 12 further comprising means for generating a control signal whenever any inhomogeneity in said test object appears in said subtractive image, said control signal activating a means for rejecting said test object.*

14. *The system of claim 12 wherein said means for causing said displacement moves said test object relative to said radiation source and said detector.*

15. *The system of claim 14 wherein said first and second images are formed by causing X-ray radiation that has passed through said test object to impinge upon phosphor means for generating corresponding first and second optical signals, said first and second optical signals being converted to said first and second electronic signals, respectively, said first and second electronic signals being digitized and stored in said first and second memory planes, respectively.*

16. *The system of claim 15 wherein one of said first and second images is subtracted from the other by computer means to produce said subtractive image.*

* * * * *